(12) United States Patent
Pancholi

(10) Patent No.: US 11,278,576 B1
(45) Date of Patent: Mar. 22, 2022

(54) METHOD OF EXTRACTING FOLLICULAR FLUID AND APPLICATION THEREOF IN TREATMENT OF VARIOUS MEDICAL CONDITIONS

(71) Applicant: Nishit Pancholi, Fremont, CA (US)

(72) Inventor: Nishit Pancholi, Fremont, CA (US)

( * ) Notice: Subject to any disclaimer, the term of this patent is extended or adjusted under 35 U.S.C. 154(b) by 294 days.

(21) Appl. No.: 16/351,498

(22) Filed: Mar. 12, 2019

Related U.S. Application Data

(60) Provisional application No. 62/641,853, filed on Mar. 12, 2018.

(51) Int. Cl.
*A61K 35/54* (2015.01)
*A61K 9/00* (2006.01)
*A61K 9/19* (2006.01)
*A61K 9/06* (2006.01)

(52) U.S. Cl.
CPC ............ *A61K 35/54* (2013.01); *A61K 9/0014* (2013.01); *A61K 9/0019* (2013.01); *A61K 9/06* (2013.01); *A61K 9/19* (2013.01)

(58) Field of Classification Search
CPC .................................................... A61K 35/54
See application file for complete search history.

(56) References Cited

FOREIGN PATENT DOCUMENTS

| EP | 0262802 A2 | * | 4/1988 |
| EP | 2022847 A1 | * | 2/2009 |
| WO | WO2016187013 A1 | * | 11/2016 |

OTHER PUBLICATIONS

Zamah (Proteomic analysis of human follicular fluid from fertile women, Clinical Proteomics, 2015, 12:5) (Year: 2015).*
Vincenti (Using Inhibitors of Metalloproteinases to treat Arthritis, Review, Arthritis and Rheumatism, vol. 37, No. 8, Aug. 1994) (Year: 1994).*
Sterlitech (https://www.sterlitech.com/blog/post/defining-a-pore-size-and-sterile-filtering-0-2-microns-vs-0-22-microns-whats-the-difference) Jun. 26, 2014 (Year: 2014).*
Zamah (Proteomic analysis of human follicular fluid from fertile women, Clinical Proteomics, 2015, 12:5) Table of proteins list (Year: 2015).*

* cited by examiner

*Primary Examiner* — Susan Hoffman
*Assistant Examiner* — Jacob A Boeckelman
(74) *Attorney, Agent, or Firm* — Steven Ivy P.C.

(57) ABSTRACT

Disclosed is a method of extracting follicular fluid from a Graafian Follicle, from a human, female donor, and conversion thereof into different forms of medications. The invention also teaches various methods of administering said medications to patients, both male and female, aesthetic rejuvenations and/or suffering from a wide variety of medical conditions, including but not limited to systemic acute and chronic diseases.

15 Claims, 12 Drawing Sheets

TABLE 1
Mean values, standard error and standard variation of the cytokines and chemokines detected in individual FF samples with the Luminex technology (bead-based multiplex sandwich immunoassays)

| Cytokines/chemokines (pg/ml) | Mean  | Standard deviation | Standard error |
|---|---|---|---|
| IL-1Ra    | 225    | 530   | 46    |
| IL-2      | 8      | 5.8   | 0.5   |
| IL-4      | 1.8    | 0.7   | 0.06  |
| IL-6      | 21.2   | 79    | 6.8   |
| IL-8      | 399    | 2785  | 241   |
| IL-9      | 9.9    | 13.4  | 1.16  |
| IL-10     | 4.6    | 4.6   | 0.4   |
| IL-12     | 15.3   | 6.2   | 0.53  |
| IL-13     | 4.5    | 0.73  | 0.064 |
| IL-15     | 1.77   | 3.76  | 0.32  |
| IFN-γ     | 32.9   | 43.1  | 3.7   |
| G-CSF     | 21.06  | 4.64  | 0.40  |
| GM-CSF    | 25.4   | 11.1  | 0.96  |
| VEGF      | 12 616 | 13 565| 1176  |
| PDGF      | 248.8  | 1388  | 120   |
| FGF       | 19     | 47.6  | 4.1   |
| IP-10     | 2083   | 1948  | 168.9 |
| MCP-1     | 296.8  | 1568  | 135   |
| CCL5      | 449    | 1087  | 94    |
| Eotaxin   | 138    | 103   | 8.9   |
| MIP-1 beta| 266    | 1989  | 172   |
| LIF       | 954    | 1150  | 103   |

FIG. 7

TABLE 2-A
Follicular Fluid proteins with functional roles in signaling

| Accession | Gene Name | Protein Name |
|---|---|---|
| IGF related | | |
| P35858 | IGFALS | Insulin-like growth factor-binding protein complex acid labile subunit |
| P05019 | IGF1 | Insulin-like growth factor 1 |
| P01344 | IGF2 | Insulin-like growth factor II |
| P08833 | IGFBP1 | Insulin-like growth factor-binding protein 1 |
| P18065 | IGFBP2 | Insulin-like growth factor-binding protein 2 |
| P17936 | IGFBP3 | Insulin-like growth factor-binding protein 3 |
| P22692 | IGFBP4 | Insulin-like growth factor-binding protein 4 |
| P24593 | IGFBP5 | Insulin-like growth factor-binding protein 5 |
| P24592 | IGFBP6 | Insulin-like growth factor-binding protein 6 |
| Q16270 | IGFBP7 | Insulin-like growth factor-binding protein 7 |
| Q13219 | PAPPA | Pappalysin-1 |

FIG. 8

TABLE 2-B
Follicular Fluid proteins with functional roles in signaling

| Accession | Gene Name | Protein Name |
|---|---|---|
| Metalloproteinase related | | |
| P08253 | MMP2 | 72 kDa type IV collagenase |
| P14780 | MMP9 | Matrix metalloproteinase-9 |
| Q9UHI8 | ADAMTS1 | A disintegrin and metalloproteinase with thrombospondin motifs 1 |
| Q76LX8 | ADAMTS13 | A disintegrin and metalloproteinase with thrombospondin motifs 13 |
| Q6UY14 | ADAMTSL4 | ADAMTS-like protein 4 |
| Q96KN2 | CNDP1 | Beta-Ala-His dipeptidase |
| P15169 | CPN1 | Carboxypeptidase N catalytic chain |
| P01033 | TIMP1 | Metalloproteinase inhibitor 1 |
| P16035 | TIMP2 | Metalloproteinase inhibitor 2 |
| O95980 | RECK | Reversion-inducing cysteine-rich protein with Kazal motifs |

FIG. 9

TABLE 2-C
Follicular Fluid proteins with functional roles in signaling

| Accession | Gene Name | Protein Name |
|---|---|---|
| Anti-apoptotic | | |
| P99999 | CYCS | Cytochrome c |
| P81605 | DCD | Dermcidin |
| Q9Y4L1 | HYOU1 | Hypoxia up-regulated protein 1 |
| P02750 | LRG1 | Leucine-rich alpha-2-glycoprotein |
| P83110 | HTRA3 | Probable serine protease HTRA3 |
| P49908 | SEPP1 | Selenoprotein P |

FIG. 10

TABLE 2-D
Follicular Fluid proteins with functional roles in signaling

| Accession | Gene Name | Protein Name |
|---|---|---|
| Other growth factor & related | | |
| P15514 | AREG | Amphiregulin |
| Q9Y5C1 | ANGPTL3 | Angiopoietin-related protein 3 |
| P01019 | AGT | Angiotensinogen |
| Q9Y4P8 | CLSTN1 | Calsyntenin-1 |
| Q16627 | CCL14 | C-C motif chemokine 14 |
| P26992 | CNTFR | Ciliary neurotrophic factor receptor subunit alpha |
| Q6UXD1 | CRELD1 | Cysteine-rich with EGF-like domain protein 1 |
| Q9UBP4 | DKK3 | Dickkopf-related protein 3 |
| Q13822 | ENPP2 | Ectonucleotide pyrophosphatase/phosphodiesterase family member 2 |
| Q8N441 | FGFRL1 | Fibroblast growth factor receptor-like 1 |
| Q9Y625 | GPC6 | Glypican-6 |
| P10912 | GHR | Growth hormone receptor |
| Q04756 | HGFAC | Hepatocyte growth factor activator |
| P08581 | MET | Hepatocyte growth factor receptor |
| P26927 | MST1 | Hepatocyte growth factor-like protein |

FIG. 11

TABLE 2-E
Follicular Fluid proteins with functional roles in signaling

| Accession | Gene Name | Protein Name |
|---|---|---|
| Other growth factor & related | | |
| P07333 | CSF1R | Macrophage colony-stimulating factor 1 receptor |
| P10721 | KIT | Mast/stem cell growth factor receptor |
| Q7Z7M0 | MEGF8 | Multiple epidermal growth factor-like domains protein 8 |
| O14786 | NRP1 | Neuropilin-1 |
| P30086 | PEBP1 | Phosphatidylethanolamine-binding protein 1 |
| P36955 | SERPINF1 | Pigment epithelium-derived factor |
| Q99435 | NELL2 | Protein kinase C-binding protein NELL2 |
| Q9HCB6 | SPON1 | Spondin-1 |
| Q03167 | TGFBR3 | Transforming growth factor beta receptor type 3 |
| Q15582 | TGFBI | Transforming growth factor-beta-induced protein ig-h3 |
| P35590 | TIE1 | Tyrosine-protein kinase receptor Tie-1 |
| P30530 | AXL | Tyrosine-protein kinase receptor UFO |
| P35916 | FLT4 | Vascular endothelial growth factor receptor 3 |
| Q6EMK4 | VASN | Vasorin |

FIG. 12

METHOD OF EXTRACTING FOLLICULAR FLUID AND APPLICATION THEREOF IN TREATMENT OF VARIOUS MEDICAL CONDITIONS

RELATED PATENT APPLICATION

The present Non-Provisional U.S. Patent application claims priority under 35 U.S.C. § 119(e) to U.S. Provisional Patent Application No. 62/641,853, titled METHOD OF EXTRACTING FOLLICULAR FLUID AND APPLICATION THEREOF IN TREATMENT OF VARIOUS MEDICAL CONDITIONS, filed on Mar. 12, 2018, the subject matter of which is incorporated herein by reference.

FIELD OF THE INVENTION

The present invention addresses the general field of medicinal substances, administrable to human beings, incorporating growth factors, hormones, steroids, vitamins and follicular fluid stem cells.

BACKGROUND OF THE INVENTION

Information Regarding Follicular Fluid and its Source

The present invention teaches a method of extracting follicular fluid ("FF") from a Graafian Follicle, from a human, female donor, and conversion thereof into different forms of medications. The invention also teaches various methods of administering said medications to patients, both male and female, aesthetic rejuvenations and/or suffering from a wide variety of medical conditions, including but not limited to systemic acute and chronic diseases.

THE FIRST SOURCE. Follicular fluid may be obtained from human, female ovarian follicles, during the naturally occurring reproductive process. Ovarian follicles are the basic unit for human reproduction. The primary follicle consists of a primary oocyte with a single layer of follicular cells. As development proceeds, the number of follicular cells increases by mitosis forming several layers around the primary oocyte. The primary follicle becomes a secondary follicle which is surrounded by the several layers of follicular cells, now collectively called the membrana granulosa which begin to secrete follicular fluid that gradually fills the inner part of the follicle.

Typically in women during each menstrual cycle one Graafian follicle develops which is a mature vesicular follicle having a diameter of about 20 mm and has a relatively high fluid pressure. The size of the fully-grown Graafian follicle varies widely between species, the volume being determined largely by the amount of follicular fluid.

During ovulation the outer layer of the follicle ruptures and the oocyte is pushed out, ready to be fertilized by a sperm. The fluid in the follicle can be aspirated or recovered from the follicle before or after expulsion of the oocyte and frozen. This is one source of obtaining follicular fluid.

THE SECOND SOURCE. Another source, which is a more robust source of obtaining follicular fluid, is during in-vitro fertilization (IVF) procedure. During the process of in-vitro fertilization for women, as a routine practice the ovaries are stimulated by gonadotrophins to develop and mature as many follicles as possible. The development of the follicles in the ovary is monitored by ultrasound. When the follicles are mature enough according to size on the ultrasound and according to the estradiol level measured in the blood, the oocytes are manually aspirated from the follicles by a technique called Transvaginal oocyte retrieval (TVOR) also known as Ovum Pick-Up (OPU). Follicular fluid which comes out in the aspirate is typically discarded since there is no use of the follicular fluid in further IVF procedure once the oocyte is aspirated. The FF obtained is typically a sterile fluid which can be obtained and frozen.

SUMMARY OF THE INVENTION

The following is intended to be a brief summary of the invention and is not intended to limit the scope of the invention:

The present invention discloses a method of extracting follicular fluid from a Graafian Follicle, and methods of utilizing said follicular fluid in healing sicknesses and injuries, as well as aesthetic and supplement applications.

The invention comprises of three functional segments: 1) method of extraction of the follicular fluid from a human donor; 2) methods of converting the extract follicular fluid into medications; 3) methods of administering said medications to human patients, both females and males.

Accordingly, the invention addresses methods of converting the extracted follicular fluid from a human, female donor, into different forms of medications, such as liquid, powered and various forms of topical medications.

The invention also discloses various methods of applying/administering said medication to patients suffering from a wide variety of medical conditions, including but not limited to systemic acute and chronic diseases.

BRIEF DESCRIPTION OF THE DRAWINGS

The components shown in the drawings are not to scale. In the interest of clarity, some of the components might be shown in a generalized form and could be identified utilizing commercial designations. All components, including its essential features, have been assigned reference numbers that are utilized consistently throughout the descriptive process outlined herein:

FIG. 7 is a table, showing the mean values, standard error and standard variation of the cytokines and chemokines detected in individual follicular fluid samples with the Luminex technology (bead-based multiplex sandwich immunoassays), in accordance with an exemplary embodiment of the present invention;

FIG. 8 is a table, showing follicular fluid proteins, related to IGF, with functional roles in signaling and in accordance with an exemplary embodiment of the present invention;

FIG. 9 is a table, showing follicular fluid proteins, metalloproteinase related, with functional roles in signaling, in accordance with an exemplary embodiment of the present invention;

FIG. 10 is a table, showing follicular fluid proteins, anti-apoptotic related, with functional roles in signaling, in accordance with an exemplary embodiment of the present invention;

FIG. 11 is a table, showing follicular fluid proteins with functional roles in signaling and related to various other growth factors, in accordance with an exemplary embodiment of the present invention;

FIG. 12 is a continuation of the table 11, in accordance with an exemplary embodiment of the present invention.

DESCRIPTIVE KEY

100—Mature Vesicular Follicle
  110—Follicular Fluid
  120—Follicular Cells
  130—Membrane
  140—Theca Interna
  150—Theca Externa
  160—Oocyte (primary follicle)
  170—Membrana Granulosa
200—Follicular Fluid Processing
  210—Natural Reproductive Process
    211—Step 1—Primordial Follicle
    212—Step 2—Primary Follicle
    213—Step 3—Secondary Follicle
    214—Step 4—Mature Follicle
    215—Step 5—Ovulation
    216—Step 6—Follicle Degeneration
  220—In-Vitro Fertilization Process
    221—Step 1—Sperm Collection and Cycle Monitoring
    222—Step 2—Ovulation Induction
    223—Step 3—Egg (Oocyte) Retrieval
    224—Step 4—Egg Fertilization
    225—Step 5—Embryo Transfer
    226—Step 6—Embryo Implantation
  230—Method of Extraction of Follicular Fluid
    231—Aspirate Follicular Fluid
    232—Centrifugation of Follicular Fluid
    233—Filtration of Follicular Fluid
    234—Lyophilization of Follicular Fluid
    235—Sterilization of Follicular Fluid
300—Processed Follicular Fluid and its Possible Forms
  301—Liquid (syrups and other solutions)
  302—Powder
  303—Tablets
  304—Capsules
  305—Topical Medication
  306—Suppositories
  307—Drops
  308—Inhalers
  309—Injections
  310—Patches
  311—Buccal and Sublingual Medications
400—Application Methods (Administration of Follicular-Fluid-Based Medicine)
  401—Oral Application
  402—Injection Application
  403—Sublingual and Buccal Application
  404—Rectal and Vaginal Application
  405—Ocular Application
  406—Ocular and Otic Application
  407—Nasal Application
  408—Inhalation Application
  409—Nebulization Application
  410—Cutaneous Application
  411—Transdermal Application
500—Medical Issues
  510—Healing Applications
    511—Systemic Acute and Chronic Diseases
    512—Wound Healing
    513—Post-Surgical Recovery
    514—Sports Injuries
    515—Musculoskeletal Injuries
    516—Dental Procedures
    517—Sexual Health Rejuvenation (male and female)
  520—Aesthetic Applications
    521—Topical and Systemic Formulations for Anti-Aging
    522—Skin Rejuvenation
    523—Hair Re-Growth
    524—Breast Rejuvenation
  530—Supplemental and Laboratory Applications
    531—Media Supplement for In-Vitro Maturation Process
    532—Additive for Culture Medium

DETAILED DESCRIPTION OF THE PREFERRED EMBODIMENT

Figure 1:
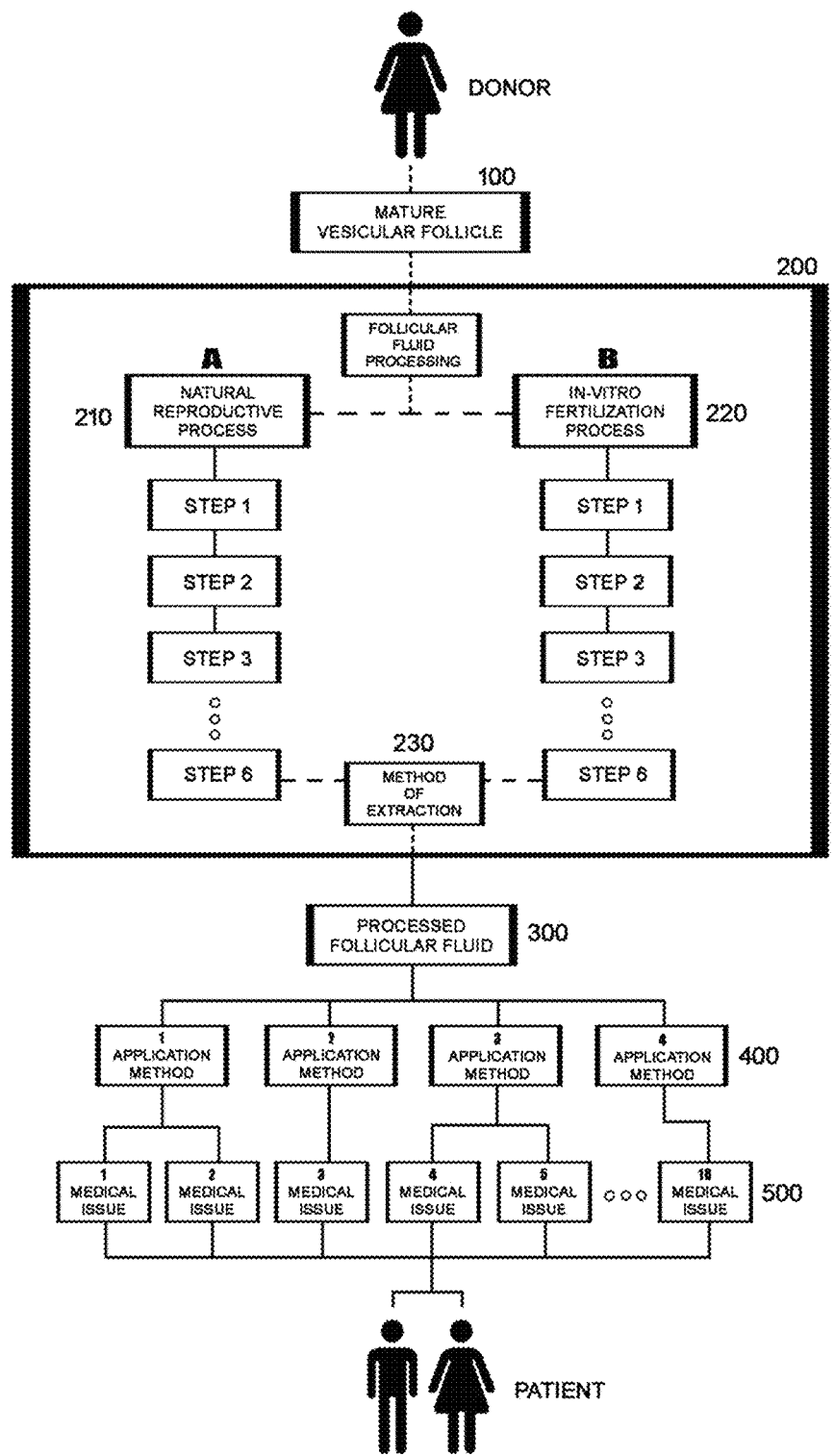
FIG. 1 is a diagram outlining the method of extracting follicular fluid and application thereof for treatment of various medical conditions, in accordance with an exemplary embodiment of the present invention.

The following description references to the above-defined drawings and represents only an exemplary embodiment of the invention. It is foreseeable, and recognizable by those skilled in the art, that various modifications and/or substitutions to the invention could be implemented without departing from the scope and the character of the invention:

As shown in FIG. 1, the present invention comprises of three functional segments: 1) method of extracting the follicular fluid from a female, human donor 230; 2) methods of converting the extract follicular fluid into medications 300; 3) uses and methods of administering said medications to human patients 400, both females and males.

1. Method of Extracting the Follicular Fluid from a Female, Human Donor 230.

Figure 2:
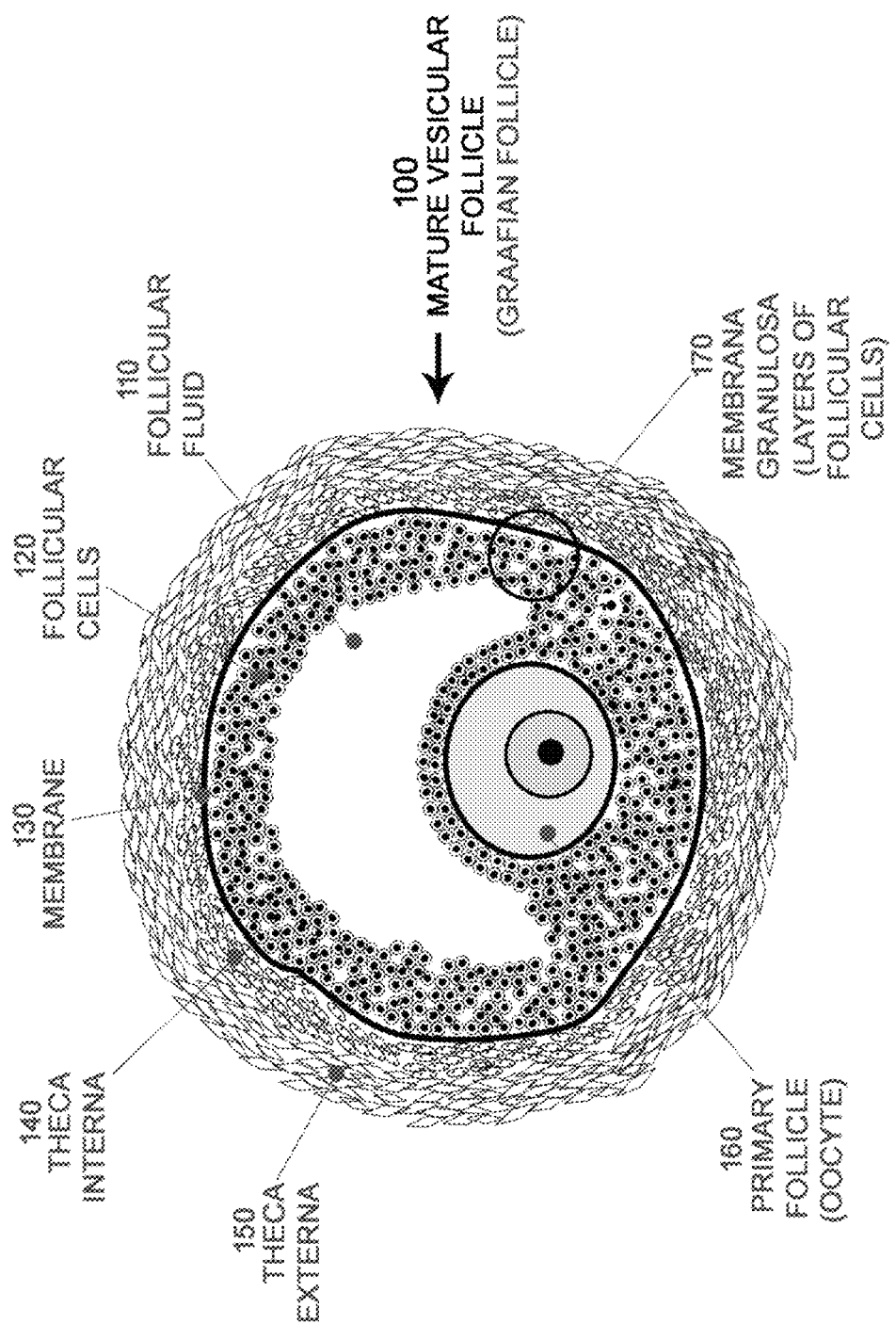
FIG. 2 is a graphical illustration depicting a Mature Vesicular Follicle, also known as the Graafian Follicle, showing its internal structure, and emphasizing the location of the follicular fluid, and its surrounding components, in accordance with an exemplary embodiment of the present invention.

The follicular fluid is extracted from a mature vesicular follicle 100, also known as the Graafian follicle. As shown in FIG. 2, the follicle contains follicular cells 120, membrane 130, theca interna 140, theca externa 150, oocyte (primary follicle) 160 and membrana granulosa 170.

Figure 3:
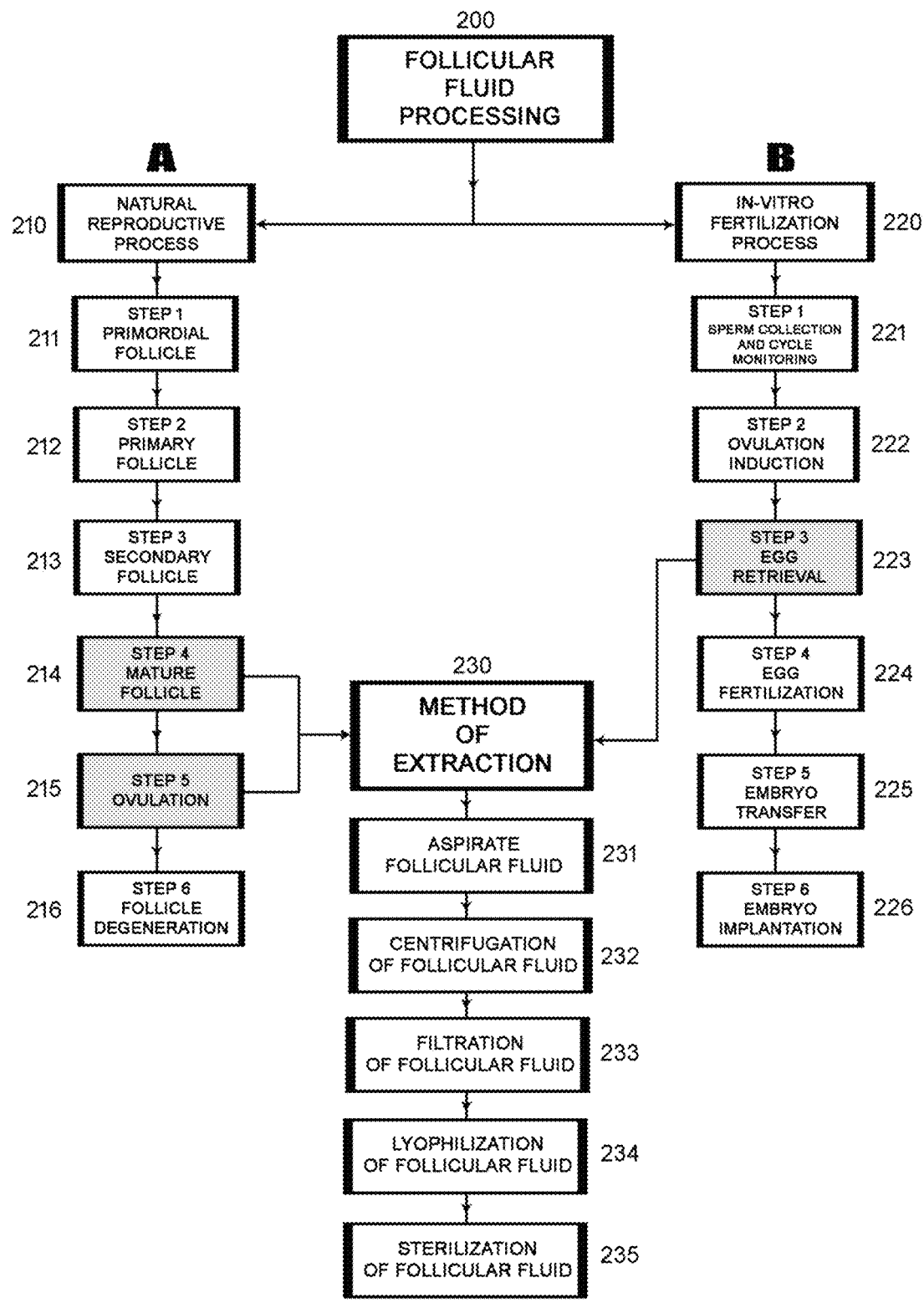
FIG. 3 is a flowchart diagram, focusing on the follicular fluid processing, outlining the source of the follicular fluid within the steps of the natural reproductive process, and/or the in-vitro fertilization process, and listing the steps comprising the method of converting the follicular fluid into a usable medical compound, in accordance with an exemplary embodiment of the present invention.

As shown in FIG. 3, the follicular fluid 110 can be extracted from the donor, undergoing a natural reproductive process 210 (Option A), or during the in-vitro fertilization process 220 (Option B).

Figure 4:
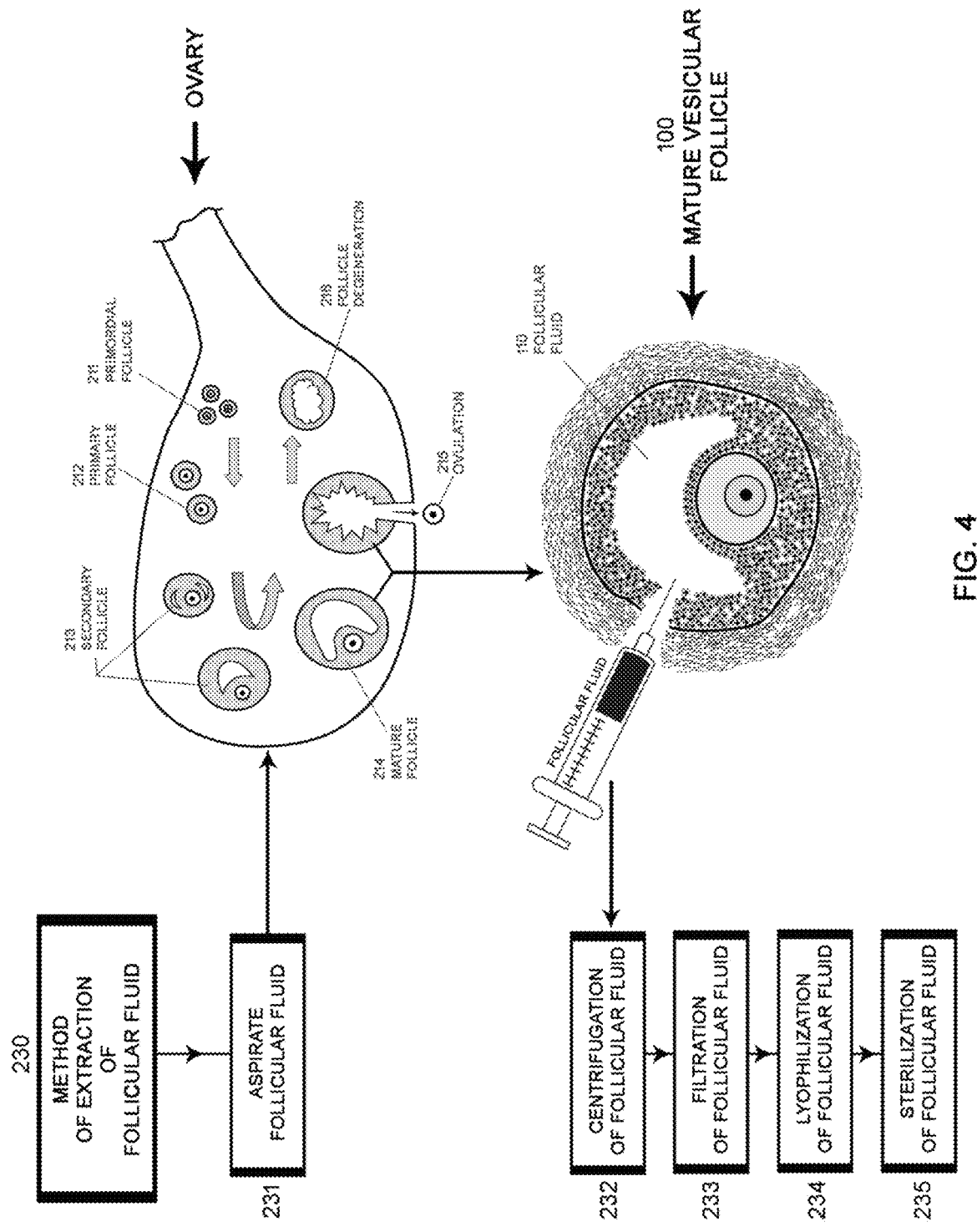
FIG. 4 is a flowchart diagram incorporating two graphical illustrations, listing the applicable processing steps, including the source and the evolution of a mature follicle, and the means of extracting the follicular fluid form said mature follicle, in accordance with an exemplary embodiment of the present invention.

During the natural reproductive process 210, the follicular fluid is secreted directly from the donor's mature follicle 214, or during the process of ovulation 215 (reference FIG. 4). Extraction of the follicular fluid from the donor during the in-vitro fertilization process 220, is conducted during the egg retrieval step 223, preceding the egg fertilization step 224.

The obtained follicular fluid 110 is a slightly viscous, straw-colored solution with a pH be above 7-0, and similar to plasma. Follicular fluid 110 is composed partly of secretions from the follicle 160, and partly of exudates from plasma. Its composition reflects changes in the secretory processes of the granulosa layer 170 and theca interna 140, and alterations in the components of plasma due to physiological processes.

Once the follicular fluid has been aspired, via the defined herein steps 214, 215 or 223, the follicular fluid 110 undergoes processing and purification 230, reverenced in FIGS. 3 and 4. Here, the follicular fluid is centrifuged 232, filtrated 233, and may undergo lyophilization 234 and sterilization 235.

2) Methods of Converting the Extract Follicular Fluid into Medications 300.

Due to its physical characteristics, the processed follicular fluid 110, available post processing step 234 and/or 235, may be converted into medications of different forms and textures 300.

The possible forms of medications 300 derived from the processed follicular fluid 110 include, but are not limited to: liquid (syrups and other solutions) 301, powder 302, tablets 303, capsules 304, topical medication 305, suppositories 306, drops 307, inhalers 308, injections 309, patches 310, buccal and sublingual medications 311.

3) Uses and Methods of Administering Said Medications to Human Patients 400, Both Females and Males.

Follicular fluid 100 is a complex of components of serum and follicular synthesized secretions, with primary components including, but not limited to: A) inorganics; B) steroids; C) hormones; D) growth factors; E) cytokines and interleukins; F) proteins, peptides and amino-acids.

A) Inorganic components. The levels of various elements in follicular fluid are close to those found in serum. Levels of vitamin C in bovine follicular fluid consistently greater than in serum.
  B) Steroids. A wide variety of steroids including estrogens, androgens and progestogens has been identified in follicular fluid.
  C) Hormones. High follicular fluid concentrations of Follicle stimulating hormone (FSH), Luteinizing hormone (LH), and Human Chorionic Gonadotrophin (hCG) have been reported. Growth Hormone (GH) has been identified in follicular fluid.
  D) Growth Factors. High levels of inhibin A and B have been identified in follicular fluid. High Bone morphogenetic protein-15 (BMP-15) were observed in the follicular fluid. Insulin-like growth factors I and II (IGF-I and -II) and IGF-binding proteins (IGFBP-3 and IGFBP-4) are high in follicular fluid. Vascular Endothelial Growth Factor (VEGF), basic fibroblast growth factor (bFGF), angiogenin and Epidermal Growth Factor (EGF) are high in follicular fluid. Granulocyte-Colony stimulating factor (G-CSF) concentrations are much higher in follicular fluid than in serum.
    IGF-1 in follicular fluid was 129+/−67 ng/ml.
    The mean concentration of iGFBP-3 was 1403±812 ng/ml.
    Adrenomedullin 402±26.46 pg/ml
    VEGF 3057±217.88 pg/ml
  E) Cytokines and Interleukins. LIF, IL-1Ra, IL-4, IL-6, IL-8, IL-10, IL-12, IL-13, G-CSF, IP-10, MCP-1, eotaxin and MIP-b Pro-inflammatory cytokines like Interleukins (IL-1beta and E2) can be found in follicular fluid (referenced in FIG. 7).
  F) Proteins, peptides and amino-acids. Follicular fluid contains several proteins that derive from blood plasma or are secreted both by granulosa and thecal cells. Most of the plasma proteins are present in follicular fluid. The follicular fluid protein-albumin concentration is higher than the respective concentrations in blood plasma. The concentration of basic amino acids is almost twice as high in the follicular fluid as in blood plasma (reference FIGS. 8, 9, 10, 11 and 12). Also, the follicular fluid total antioxidant capacity (TAC) was found to be significantly higher.

The potential uses and the application methods of the processed follicular fluid 300 are wide ranging. For example, when used in liquid form 301, after centrifugation 232 (removing cellular content), filtration 233 and sterilization 235, the follicular fluid 300 may utilized as: 1) an effective media supplement for in-vitro maturation as it influences the ability of in vitro-matured oocyte to acquire developmental competence; 2) as an additive for culture medium which improves the maintenance and differentiation of different cell types in culture.

Figure 6:
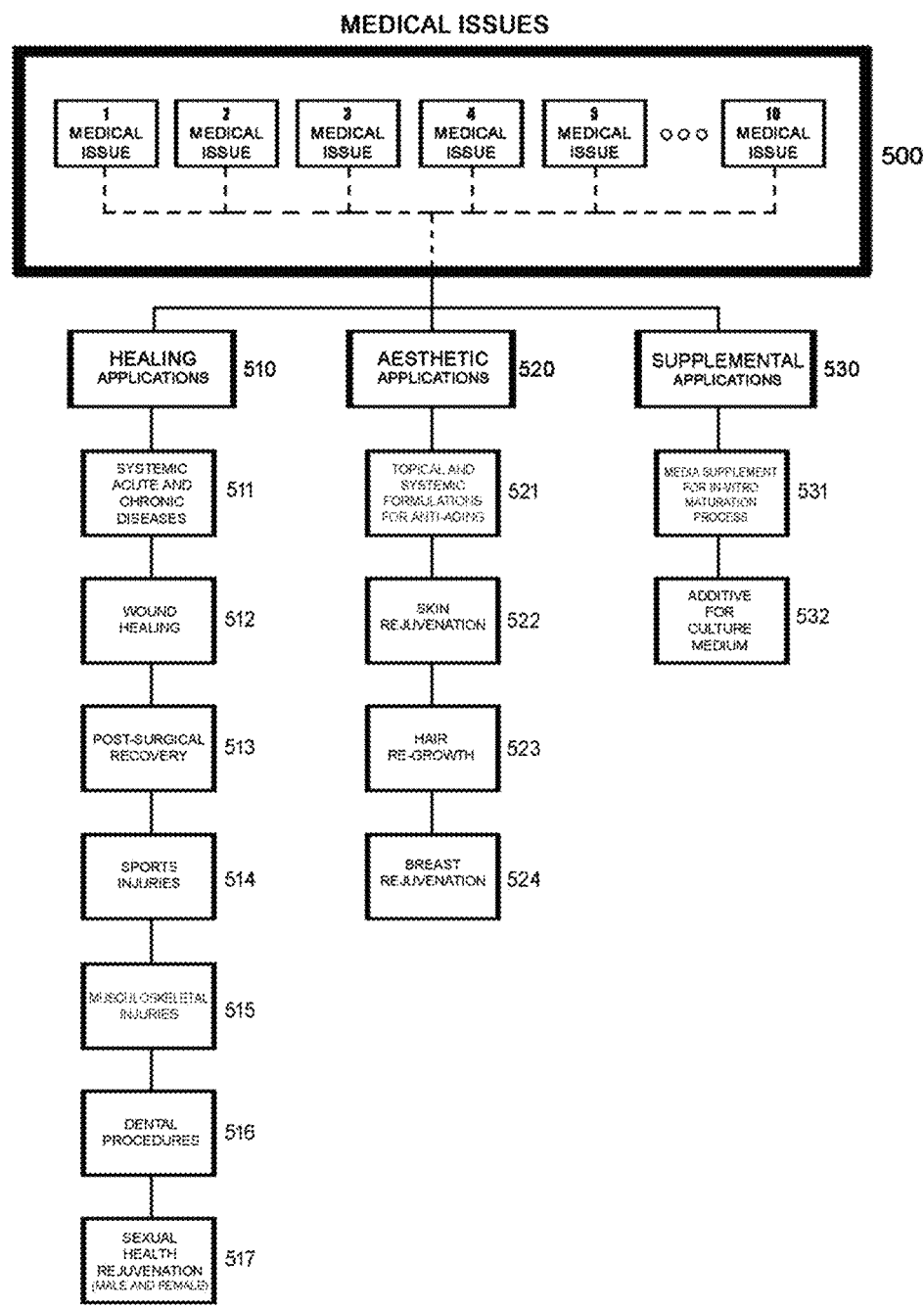
FIG. 6 is a flowchart outlining various medical issues which could be cured by application of the follicular fluid, wherein said flowchart subdivides the medical issues into three sub-categories, including (1) healing, (2) aesthetic and (3) supplemental applications of the follicular fluid, in accordance with an exemplary embodiment of the present invention.

Potential uses of follicular fluid 300 in lyophilized form (after filtration 233, lyophilization 234 and sterilization 235, providing freeze-dried powder form) include: 1) an allogenic source of growth factors and cytokines for accelerated healing in (a) medical/healing applications 510 (systemic acute and chronic diseases 511, wound healing 512, post-surgical recovery 513, sports injuries 514, musculoskeletal injuries 515, dental procedures 516, sexual health rejuvenation for both males and females 517); (b) aesthetic applications 520 (topical and systemic formulations for anti-aging 521, skin rejuvenation 522, hair re-growth 523, breast rejuvenation 524 etc.) referenced in FIG. 6.

Figure 5:
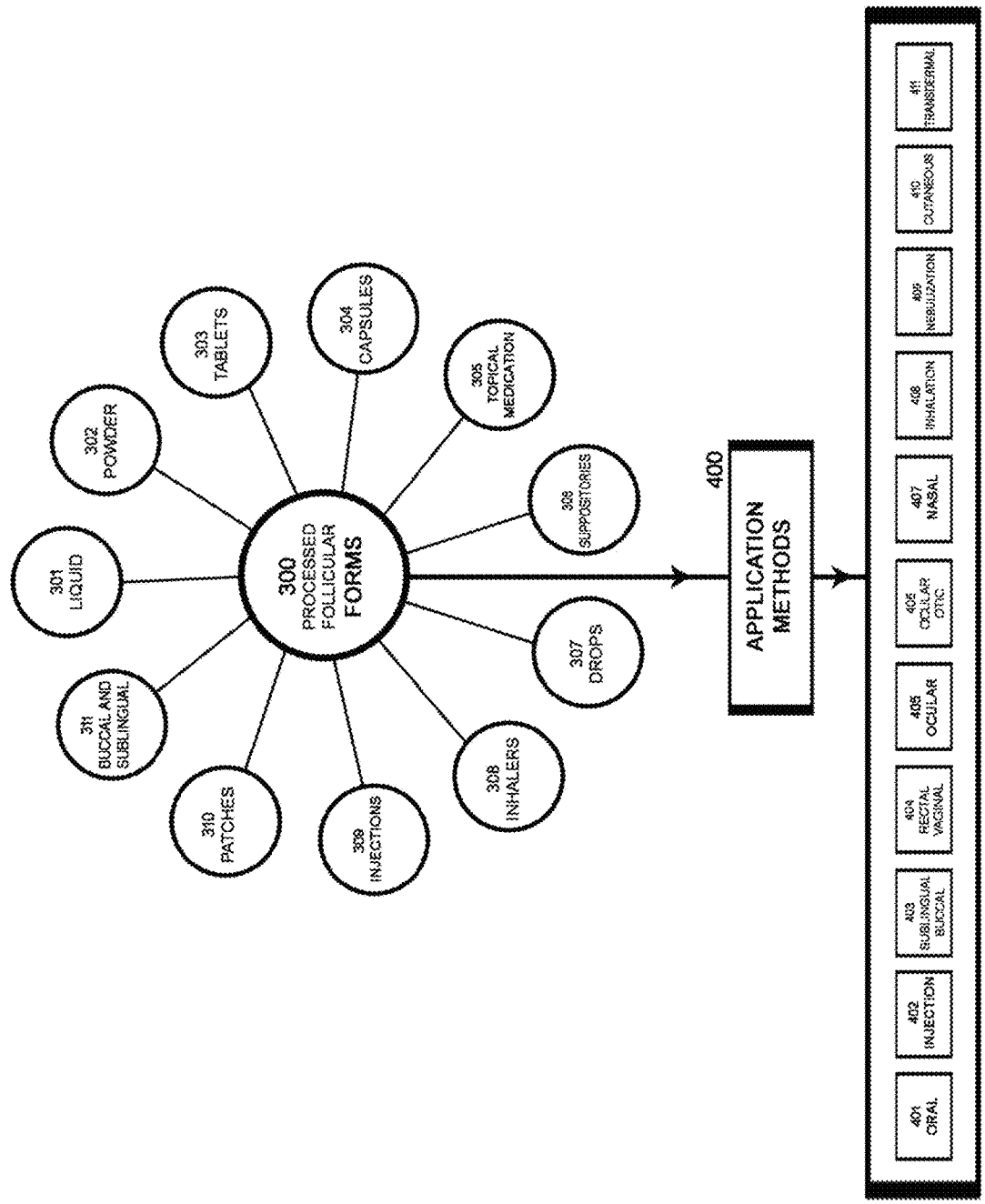
FIG. 5 is a diagram outlining the possible physical form of the processed follicular fluid, along with their possible methods of application to the patient, in accordance with an exemplary embodiment of the present invention.

Methods of administrating said follicular fluid-derived medications of to the female/male patients include: oral application 401, injection application 402, sublingual and buccal application 403, rectal and vaginal application 404, ocular application 405, ocular and otic application 406, nasal application 407, inhalation application 408, nebulization application 409, cutaneous application 410, transdermal Application 411 (referenced in FIG. 5).

In summary, the extracted follicular fluid 110 can generally be used for medical, and cosmetic applications (a) as a source for growth factor and cytokine treatments; (b) as topical and systemic formulations for cosmetic use as anti-aging injections, or creams; (c) as dressings for accelerating healing of skin injuries and surgical wounds; or (d) as systemic treatment of acute and chronic diseases.

The extracted follicular fluid 110 can be used for application (a) as is after centrifugation; (b) as a lyophilized product (freeze drying, also known as lyophilisation or cryodesiccation, is a low temperature dehydration process) the follicular fluid is biologically more stable at room temperature, but is usable only upon re-constitution with water for application (injection or topical); (c) or stem cells extracted from the follicular fluid (by centrifugation).

The follicular fluid 110 is cleaned once by the process of centrifugation 232. Here, the follicular fluid centrifuged 232 for 20 minutes, at 3300 rpm, separating the growth factors and the cytokines from debris, creating a supernatant containing said growth factors and said cytokines. The supernatant is then aspirated and ready for use. The follicular fluid 110 can be further cleaned by the process of filtration 233. Here, following the aspiration process, the follicular fluid 100 if passed through a 0.2 micron filter.

The follicular fluid 110 can be (a) stored at room temperature if used within 4 hours; (b) stored in refrigerator for use within 48 hours; or (c) stored in freezer if to be used after 48 hours.

If the follicular fluid (or supernatant) has been lyophilized, the final product has been converted into powder (powdered supernatant). To use said powdered supernatant on a patient, the powder must be thawed back to room temperature, and subsequently reconstituted by mixing said power supernatant with water. The lyophilized form of the follicular fluid is prepared by freeze drying the follicular fluid. The lyophilized powder contains mostly growth factors.

The medical or cosmetic personnel will re-constitute the lyophilized powder by adding to the powder a fixed amount of water for injection with the help of a syringe and a needle from a separate vial (supplied with the preparation). Then they will invert the vial 2-3 times to re-suspend the powder, until all the powder is dissolved. Then this re-constituted follicular fluid will be taken in a syringe for injection in the patient.

One example of the lyophilized follicular fluid powder is in the use as a source of growth factors and cytokines for degenerative osteoarthritis of the knee joint. The medical professional will be supplied with vial of lyophilized follicular fluid powder and about 5 cc of water for injection. The medical professional will aspirate about 3.5 cc of water for injection from the water vial using a syringe and needle and transfer to the vial containing the powder. The vial will be gently inverted 2-3 times to re-suspend the powder, until all the powder is dissolved. The dissolved powder should be a free of turbidity. The clear solution will then be taken in a 5 cc syringe and injected into the knee joint of the patient with or without ultrasound guidance.

I claim:

1. A method of treating body parts affected by arthritis in a patient; wherein said body parts affected by arthritis are human body parts selected from a group consisting of joints, ankles, back, knees, hips, fingers, hands, muscles, neck, wrist, legs, skin, eyes, lungs, heart, blood, and nerves;
said method comprising of administering to the patient a therapeutically effective amount of a follicular fluid isolated from a graafian follicle produced by a human ovary during ovulation and aspirated after being cleaned at least once by centrifugation, wherein the follicular fluid so obtained contains proteins and growth factors wherein said proteins comprise of cytokines and chemokines, and the method results in reduction of arthritis symptoms in the patient; wherein said cytokines and chemokines consist of LIF, IL-1Ra, IL-4, IL-6, IL-8, IL-10, IL-12, IL-13, G-CSF, VEGF, IP-10, MCP-1, eotaxin, MIP-β, IL-15, GM-CSF, CCL5, PDGF, IFN-γ, IL-9, IL-2 and FGF; wherein said centrifugation requires placement of the follicular fluid into a centrifuge and centrifugation of said follicular fluid at 3300 RPM for at least 20 minutes separating the growth factors and the cytokines from debris, creating a supernatant containing said growth factors and said cytokines; wherein said supernatant is put through the process of lyophilization transforming said supernatant into a powered supernatant, thereby extending the supernatant's longevity; and wherein said powdered supernatant is reconstituted for usages on a patient by mixing said powered supernatant with water.

2. The method of claim 1, wherein said administering to the patient said therapeutically effective amount of the follicular fluid is done by injecting the arthritis affected body part with a needle attached to a syringe.

3. The method of claim 1, wherein said administering to the patient said therapeutically effective amount of the follicular fluid is done topically in a form of topical medication.

4. The method of claim 3, wherein said topical medications are selected from a group consisting of creams, foams, gels, lotions, and ointments.

5. The method of claim 1, wherein said administering to the patient said therapeutically effective amount of the follicular fluid is done via applications selected from a group consisting of systemic application, intravenous application, subcutaneous application, and intraperitoneally application.

6. The method of claim 1, wherein said isolation of the follicular fluid from the graafian follicle is done manually using a needle attached to a syringe.

7. The method of claim 1, wherein said supernatant is further purified by passing the supernatant through a 0.2 micron filter.

8. The method of claim 1, wherein said follicular fluid is aspirated using a needle attached to a syringe.

9. A method of treating conditions associated with damaged or diseased teeth, skin, hair, bone, muscle in a patient, said method comprising of administering to the patient a therapeutically effective amount of a follicular fluid isolated from a graafian follicle produced by a human ovary during ovulation and aspirated after being cleaned at least once by centrifugation, wherein the follicular fluid so obtained contains proteins and growth factors wherein said proteins comprise of cytokines and chemokines, and the method results in an improvement in the patient's condition; wherein said administering to the patient said therapeutically effective amount of the follicular fluid is done by injecting the damaged or diseased teeth, skin, hair, bone, muscle in a patient with a needle attached to a syringe; wherein said cytokines and chemokines consist of LIF, IL-1Ra, IL-4, IL-6, IL-8, IL-10, IL-12, IL-13, G-CSF, VEGF, IP-10, MCP-1, eotaxin, MIP-β, IL-15, GM-CSF, CCL5, PDGF, IFN-γ, IL-9, IL-2 and FGF; wherein said centrifugation requires placement of the follicular fluid into a centrifuge and centrifugation of said follicular fluid at 3300 RPM for at least 20 minutes separating the growth factors and the cytokines from debris, creating a supernatant containing said growth factors and said cytokines; wherein said supernatant is put through the process of lyophilization transforming said supernatant into a powered supernatant, thereby extending the supernatant's longevity; and wherein said powdered supernatant is reconstituted for usages on a patient by mixing said powered supernatant with water.

10. The method of claim 9, wherein said administering to the patient said therapeutically effective amount of the follicular fluid is done topically in a form of topical medication.

11. The method of claim 10, wherein said topical medications are selected from a group consisting of creams, foams, gels, lotions, and ointments.

12. The method of claim 9, wherein said administering to the patient said therapeutically effective amount of the follicular fluid is done via applications selected from a group consisting of systemic application, intravenous application, subcutaneous application, and intraperitoneally application.

13. The method of claim 9, wherein said isolation of the follicular fluid from the graafian follicle is done manually using a needle attached to a syringe.

14. The method of claim 9, wherein said supernatant is further purified by passing the supernatant through a 0.2 micron filter.

15. The method of claim 9, wherein said follicular fluid is aspirated using a needle attached to a syringe.

\* \* \* \* \*